US010405745B2

(12) United States Patent
Gnana et al.

(10) Patent No.: US 10,405,745 B2
(45) Date of Patent: Sep. 10, 2019

(54) HUMAN SOCIALIZABLE ENTITY FOR IMPROVING DIGITAL HEALTH CARE DELIVERY

(71) Applicant: Haranth Gnana, San Ramon, CA (US)

(72) Inventors: Haranath Gnana, San Ramon, CA (US); Kusumapriya Haranath, San Ramon, CA (US)

(*) Notice: Subject to any disclaimer, the term of this patent is extended or adjusted under 35 U.S.C. 154(b) by 290 days.

(21) Appl. No.: 15/263,260

(22) Filed: Sep. 12, 2016

(65) Prior Publication Data

US 2017/0087726 A1 Mar. 30, 2017

Related U.S. Application Data

(60) Provisional application No. 62/233,409, filed on Sep. 27, 2015.

(51) Int. Cl.
*A61B 5/00* (2006.01)
*B25J 11/00* (2006.01)
*G06F 19/00* (2018.01)
*A63H 3/00* (2006.01)
*G08B 21/04* (2006.01)
*G08B 25/01* (2006.01)
(Continued)

(52) U.S. Cl.
CPC .......... *A61B 5/0002* (2013.01); *A61B 5/6896* (2013.01); *A63H 3/003* (2013.01); *B25J 11/0005* (2013.01); *G06F 19/3418* (2013.01); *G08B 21/0423* (2013.01); *G08B 21/0461* (2013.01); *G08B 21/0469* (2013.01); *G08B 21/0476* (2013.01); *G08B 25/016* (2013.01); *G16H 40/63* (2018.01); *G16H 40/67* (2018.01)

(58) Field of Classification Search
CPC ... A61B 5/0002; A61B 5/0013; A61B 5/0022; A61B 5/6896; A63H 2200/00; A63H 3/003
See application file for complete search history.

(56) References Cited

U.S. PATENT DOCUMENTS 7,062,073 B1  6/2006  Tumey et al.
8,565,922 B2 * 10/2013  Kidd ..................... G05B 15/00
                                                  700/245
(Continued)

OTHER PUBLICATIONS www.parorobots.com/pdf/pressreleases/Paro%20found%20to%20improve%20Brain%20Function.pdf.

*Primary Examiner* — John Villecco
(74) *Attorney, Agent, or Firm* — Kevin H. Fortin

(57) ABSTRACT

A health care delivery and monitoring system including a robotic figurine with a furry layer, having components and a mechanism that facilitates robotic motion and communication. The components includes a speaker, a motor assembly, a battery, control circuitry, a video camera, speech generator, a communication interface, a network interface and a speech detector operatively connected with each other. The video camera and the wearable device cooperate to enable the robotic figurine to observe the user. The system leverages data from the various digital devices of the patients and other $3^{rd}$ party syndicated sources to derive insights and enable the delivery of personalized care to the patients. The network interface being connected via a network to a computer, which utilizes the derived insights to provide instructions to the figurine including gesture and voice commands that enable effective care delivery.

15 Claims, 5 Drawing Sheets

(51) Int. Cl.
  *G16H 40/63* (2018.01)
  *G16H 40/67* (2018.01)

(56) References Cited

U.S. PATENT DOCUMENTS

| | | | | |
|---|---|---|---|---|
| 8,588,887 B2* | 11/2013 | Arneson | ............. | A61B 5/0002 600/407 |
| D748,088 S | 1/2016 | Kidd et al. | | |
| 2002/0183598 A1* | 12/2002 | Teraura | ............... | A61B 5/0002 600/300 |
| 2005/0154265 A1* | 7/2005 | Miro | ................... | A61B 5/0002 600/300 |
| 2006/0234602 A1 | 10/2006 | Palmquist | | |
| 2007/0159779 A1 | 7/2007 | Chang | | |
| 2007/0198128 A1* | 8/2007 | Ziegler | ................... | B25J 5/007 700/245 |
| 2009/0055019 A1* | 2/2009 | Stiehl | ................... | B25J 9/1671 700/249 |
| 2012/0295510 A1* | 11/2012 | Boeckle | .................. | A63H 3/28 446/72 |
| 2013/0280985 A1* | 10/2013 | Klein | .................... | A63H 3/003 446/297 |
| 2014/0038489 A1* | 2/2014 | Sharma | .................. | A63H 30/04 446/175 |
| 2014/0203950 A1* | 7/2014 | Zdeblick | ............. | G06F 19/3418 340/870.07 |
| 2015/0138333 A1* | 5/2015 | DeVaul | ................... | G06F 3/013 348/78 |
| 2015/0238879 A1* | 8/2015 | Wu | ........................ | A63H 30/04 446/484 |
| 2016/0029962 A1* | 2/2016 | Hyde | .................... | A61B 5/117 600/301 |
| 2016/0029963 A1* | 2/2016 | Hyde | .................. | A61B 5/1171 600/301 |
| 2016/0077788 A1* | 3/2016 | Wong | .................... | A63H 30/04 704/275 |
| 2016/0174901 A1* | 6/2016 | Majic | .................. | A61B 5/6896 600/301 |
| 2018/0214784 A1* | 8/2018 | Klein | .................... | A63H 3/003 |
| 2018/0361263 A1* | 12/2018 | Boeckle | .................. | G09B 5/06 |

* cited by examiner

HUMAN SOCIALIZABLE ENTITY FOR IMPROVING DIGITAL HEALTH CARE DELIVERY

CROSS-REFERENCE TO RELATED APPLICATIONS

This patent application claims the benefit to U.S. Provisional Patent Application No. 62/233,409, filed 27 Sep. 2015, the disclosure of which is incorporated herein by reference.

FIELD OF THE INVENTION

This invention relates to virtual human companions. More particularly, this invention relates to networked virtual human companions with audio and visual communication capability that can provide healthcare delivery & monitoring as well as life style monitoring.

BACKGROUND OF THE INVENTION

A current healthcare challenge particularly in the United States, is the activity of providing healthcare to our senior citizens. The senior citizen population are expected to go up by over 50% in the next decade leading to a significant increased demand for care delivery. There are numerous inventions trying to address this problem from simple mobile apps to small specific built devices to help various aspects of managing health. Many of these have great utility and are backed with hard science, extensive studies, and research.

Implementation and management of healthcare programs, for example weight management programs, can benefit from developing data reflective of the program participants activities and habits including dietary and exercise regimes. It is found that utilizing a computer that enables a participant to record data helps a caregiver or program manager optimize program affects.

Unfortunately, participants may not be eager to record data on a continuing basis. Further, it is a well studied fact that participants' emotional states and health are relevant to the outcome of any healthcare program, including weight management. Programs that focus both on a participants emotional well-being in addition to physical well-being yields better results than focusing only on the latter.

Kidd, Cory David (February 2008) *Designing for Long-Term Human-Robot Interaction and Application to Weight Loss* (Doctoral dissertation), Massachusetts Institute of Technology, (hereinafter "Kidd") describes and supports many aspects of utilization of a social robot system for improving weight loss program deliver. The results of using this social robot system exceed the results from utilizing a computer to enter data reflective of a weight loss regime. This is due to the emotional benefit that a robotic companion provides to participants. Kidd describes the use of a small stationary humanoid type rudimentary robot that engages patients using basic audio communication techniques.

U.S. Patent Publication No. U.S. 2007/0159779 to Chang discloses a personal computer disguised as a figurine. The figurine includes motion sensors and optical sensors to detect action near the figurine. The computer includes servo motors and other devices capable of enabling responsive gestures to external stimuli.

U.S. Pat. No. 7,062,073 B1 to Tumey et al. describes a robotic toy capable of recognizing human users and inanimate objects. The robot includes the ability to recognize facial features and expressions. This enables the robot to identify and interact with particular users in unique ways.

U.S. Patent Publication No. U.S. 2006/0234602 A1 to Palmquist describes a figurine that communicates with and utilizes the processing capability of an external computer via a network. This device has expanded interactive capability including voice recognition and responsive communication because the computing capability need not be built into the figurine.

U.S. Pat. No. 8,588,887, issued on Nov. 19, 2013 to Arneson et al., discloses an ingestible sensor system that is swallowed. The sensor system includes an ingestible sensor that communicates an acoustic signal to a signal amplifier attached to the user. The amplifier communicates wirelessly to a network for communicating health and diagnostic data to a health care provider.

While these figurine robots represent advancements in the art, their design and capabilities are limited. What is desired is a robot and an entire system that enables long term interaction with a health care program participant to monitor both physical and emotional health. What is also desired is a way of providing improved life quality to participants through the use of health care monitoring and delivery at home instead of confinement in a health care facility. What is further desired is a way to improve the lives of those people, especially senior citizens suffering with memory issues, and that need companionship. A way of improving diet, lifestyle, safety, and healthcare is desired. Further, a way to enable adherence to "care plans" including those designed by care delivery professionals. What is further desired is a way of people in an extended care network including family, friends and other appropriate people is desired.

SUMMARY OF THE INVENTION

A method and system for improving health monitoring and care delivery includes providing a robotic figurine. The figurine has components including: a speaker, a motor assembly, a battery, control circuitry, a video camera, speech generator, a video display module, a communication interface, a local computer a network interface and a speech detector operatively connected with each other. The robotic figuring includes an outer layer having fir, and stuffing to protect the figurine and to enable the figurine to look and feel endearing to a user.

The video display module is a two dimensional LCD display that enables video conferencing with a health care provider, for example. In an alternate embodiment, the video display module includes a projector for projecting two dimensional images on a wall or screen in the location of a user. In a further embodiment, the video display module includes a holographic generator to communicate a three dimensional image in the location of a user.

The method collects data with the figurine. The data is used to enable intelligent communication between the figurine and the user. The data is also used to develop, implement and monitor a health care program for the user. The data collected includes biometric, speech and video data associated with the user, context data, medical record data and combinations thereof.

The care buddy figurine may not always be facing a user. The user may move about a room. Also importantly, the care buddy is portable and may be in an automobile operated by a user, where the line of sight is not direct. The care buddy can be carried by a user so that the camera needs to have peripheral video capture capability in both the horizontal plane and a vertical plan perpendicular to the floor or ground.

In one embodiment of the invention, the figurine includes two eyes, each having an embedded video camera. It is advantageous if each video camera can capture video in a peripheral viewing range of more than 180° in a horizontal plane parallel to the floor or ground at the location of a user. More preferably, the peripheral range is between 180° and 270°, or greater. In one embodiment, this is accomplished by providing convex lenses capable of improving the peripheral range of the video camera, or by providing a video camera capable of otherwise capturing the desired peripheral range.

Two or more eyes are preferable to enable the figurine to detect depth and distances.

In another embodiment, each video camera has a vertical range captured by the video camera is between 90° and 270°, or more. This is accomplished by providing convex lenses capable of improving the vertical range of the video camera, or by providing a video camera capable of otherwise capturing the desired vertical range.

In one embodiment, the eyes are equipped with a video robotic motor assembly that communicates with the control circuitry that moves the eyes to improve the vertical and peripheral perception range.

The data is associated with the user. The figurine communicates the data to the backend computing engine for processing and the backend computing engine helps the figurine generate a verbal conversation between the figurine and the user.

In one embodiment, the system includes a client interface with a video terminal in communication with the figurine to provide supplemental communication to the user. A care giver such as a physician can interact directly with the user via the client interface in real time. In this way the user communicates both with the figurine and the care giver when necessary or convenient.

In one embodiment, the video terminal streams three dimensional images, or two dimensional images. Accordingly, the client interface provides a real-looking interaction with a human care giver. Preferably, the video terminal depicts a care provider and streams a care plan including verbal communication from the care provider. The care provider utilizes at least some of the data collected with the figurine to develop and communicate the care plan.

Both the figurine and the backend computing engine leverage advanced analytics capabilities both locally and remotely to analyze data specific to the user as well as aggregate data. A firewall between the figurine and the backend computing engine can be created to protect selected private data from distribution beyond the figurine.

Ideally, the data collected with the figurine is used to detect care plan adherence, and to anticipate deviations from the care plan. In this way the care giver can optimally utilize time spent in communication with the user to address the user's needs.

The system is enabled by a local as well as a remote compute resource with advanced analytics and artificial intelligence capabilities to analyze all of the data from the user as well as the aggregated patient data across all the user population to derive actionable insights and enable the robotic figurine to deliver messages/instructions to the end user to achieve "care plan" adherence

The drawings provide various examples of how systems and methods of the present invention are configured. Further detail is provided in the detailed description. These examples provide an understanding of the invention, however the legal bounds of the invention are defined by the appended claims.

DETAILED DESCRIPTION

Figure 1:
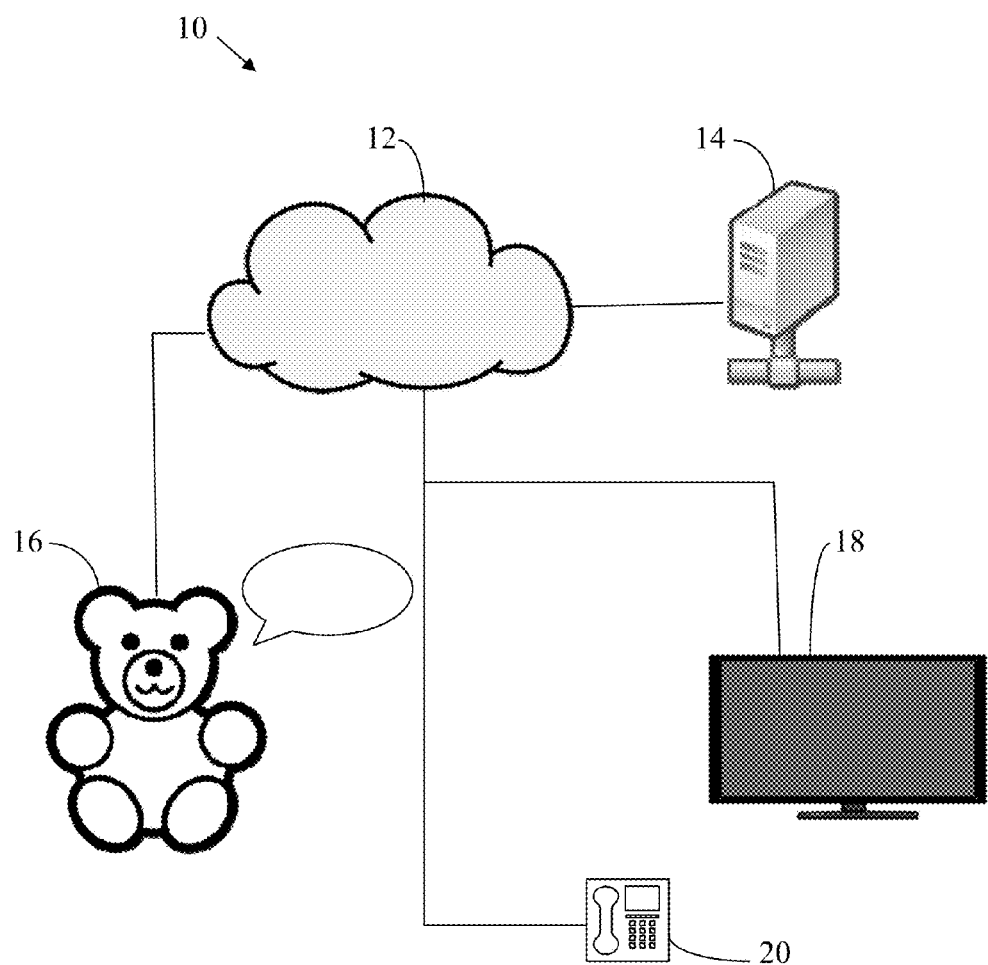
FIG. 1 is a system diagram in accordance with the present invention.

FIG. 1 shows a system, generally designated with the reference numeral 10. The system 10 includes a care buddy 16, a communications network 12, a computing resource 14, a client interface 18, and a telephonic interface 20. These system 10 elements are operatively connected with each other through the communications network 12. The care buddy 16 is a figurine such as a stuffed animal or doll that is preferably less than eighteen inches in height so that it may be easily transported or situated in a small space.

Portability of the care buddy 16 is important so that it will be moved within a home or other location of a user to facilitate emotional support and data collection. The care buddy 16 is anticipated to be a traveling companion during walks, bike rides, and automotive transport. The care buddy 16 can be transported to a health care appointment, or to any other location. It is critical that the care buddy 16 is durable and capable of withstanding drops, impact, direct sunlight and changes in temperature. The use of a stuffed animal embodiment is the perfect choice combining flexibility to be carried in a bag, backpack, on a car seat, or anywhere. The stuffing prevents impact and vibration damage, as well as heat and humidity fluctuations from damaging the care buddy 16. The care buddy 16 is also termed a "figurine" herein.

The communications network 12, includes the Internet, a private network, or a virtual private network in various embodiments of the invention. It can be appreciated that other network mechanisms, including cellular data networks, can be utilized that enable the communication of data, video, images or voice.

The backend computing engine 14 includes an array of computers or processors in one embodiment of the invention. This array may be co-located, or located at various nodes in the communications network 12. It can be appreciated that tasks such as facial feature recognition, voice recognition, context recognition, machine learning, and artificial intelligence functionality require significant computing capacity. Accordingly the backend computing engine is particularly adapted to scale computing ability during times of peak task demand in accordance with the present invention.

The telephonic interface 20 enables two way communication with a care giver having access to the system 10, and the client interface 18 enables an alternate form of communication, such as video conferencing, with a care giver having access to the system 10, a technician, or other support personnel. The client interface 18 can include any one or more of: a LCD screen, a touch screen, a video projector, a holographic projector, a wearable display, and any other visual communication device.

Figure 2:
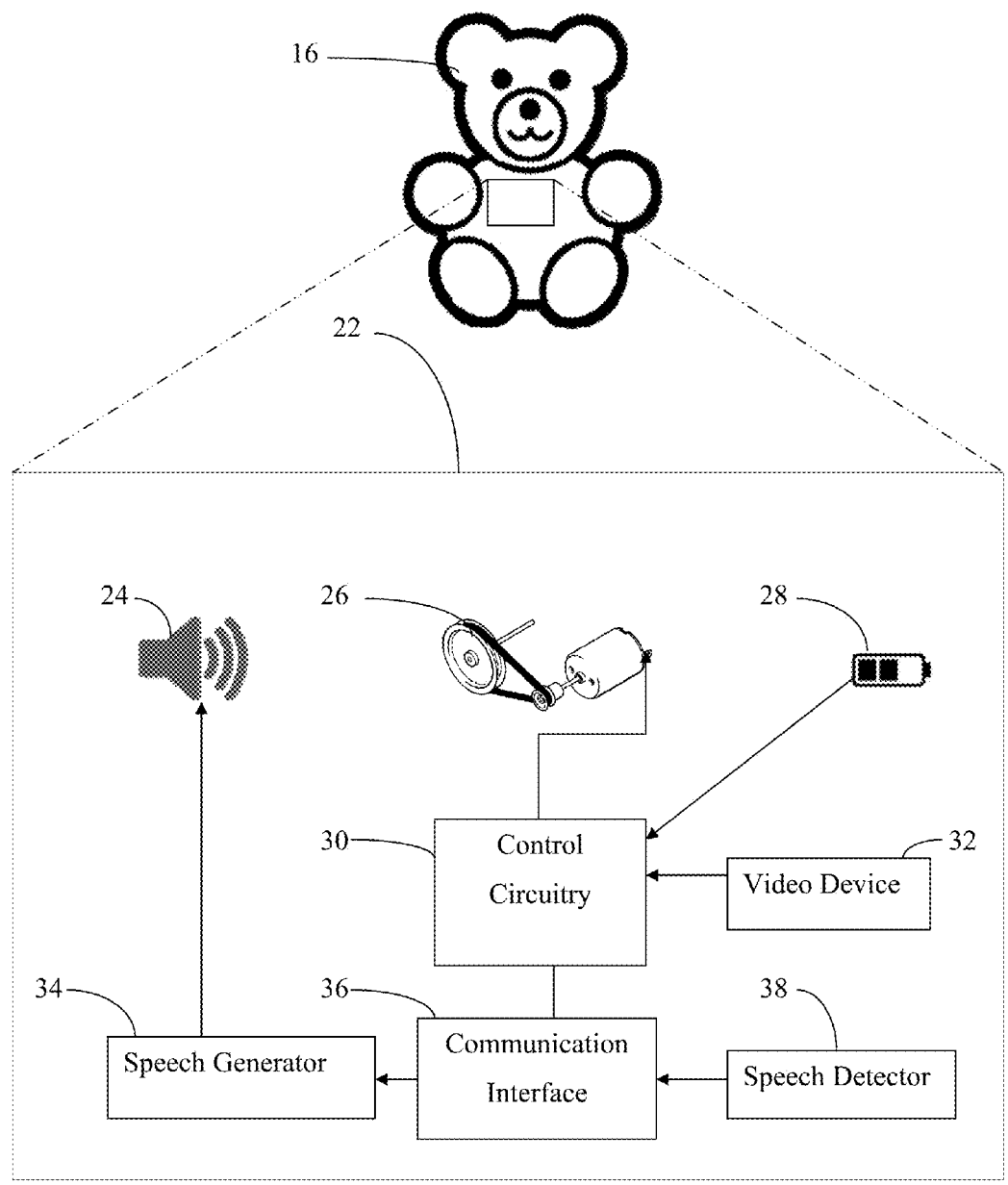
FIG. 2 is a hardware diagram in accordance with the present invention.

FIG. 2 shows the care buddy 16. The care buddy 16 is a robotic figurine equipped with a mechanism 22 to enable robotic motion, verbal communication, gestural communication, sensory perception and a local computing environment. The mechanism 22 and its elements are housed within the care buddy 16.

The mechanism 22 includes a speaker 24, a motor assembly 26, a battery 28, control circuitry 30, video device 32 such as a video camera, speech generator 34, a communication interface 36, and a speech detector 38. These elements of the mechanism 22 are operatively connected with each other within the care buddy 16.

The video device 32 includes video cameras embedded in eyes of the care buddy, or in other locations, to maximize the field of view.

The care buddy 16 in one embodiment of the invention assumes the form of a kind and loving stuffed animal. The care buddy 16 includes layers of soft insulating stuffing surrounding at least a portion of the mechanism 22.

The form of a stuffed animal has several advantages. The first advantage is that the stuffing actually protects the mechanism 22 from impact, humidity, and temperature changes. The stuffing provides the capability of utilizing the care buddy 16 in extended temperature ranges that could overheat or freeze the mechanism 22. The stuffing also provides the advantage of giving the care buddy 16 the endearing qualities of attractiveness, softness, and huggability. Further, the care buddy blends when situated in a household environment.

The care buddy 16 is transportable and can be seated in an automobile, placed in a purse, or even carried to a restaurant without the stigma and inconvenience of carrying a traditional health care monitoring machine.

In one embodiment, the care buddy 16 communicates verbally through the speaker to the user. In another embodiment the care buddy utilizes body language generated from robotic movement of appendages, the head, and eyes.

In yet another embodiment, the care buddy 16 is equipped with a video projector that can project images on any surface within a foot or more of the care buddy 16. The video projector can be connected to the system of the present invention to display video communications from a health care provider, for example. The video projector can be utilized to display other video items, including movies and internet web pages. Since the care buddy 16 is also equipped with a video camera, movements relative to the displayed image can be used to select, deselect and interact with the displayed image in a fashion similar to a touch screen or mouse enabled interface. In a variation of this embodiment, the user is equipped with sensors attached to the user's fingertips to facilitate improved recognition of user's movements relative to the displayed image. The sensors may form a ring about the user's fingertips, or some of them, and include an accelerometer and a radio frequency detection device. In a variation of this embodiment, acoustic bursts outside of the human hearing range are generated by the speaker, and a peripheral device. These acoustic bursts are reflected by objects, including the user and its hands. The acoustic bursts, sensors and video data are combined, or used independently, to determine user motion and gestures that can control the displayed image, navigate web pages, and otherwise interact with the system of the present invention.

In a variation of this embodiment, the care buddy 16 includes a waterproof layer surrounding the stuffing. The care buddy 16 also includes an outer layer formed of soft fuzzy material, such as synthetic fur. The soft fuzzy material includes a thin coating of a stain repellent so that even after extensive use the care buddy 16 can remain unsoiled. The waterproof layer, in addition to repelling water, provides a electrical insulating shield to inhibit electrical current flowing out from the care buddy 16, and to inhibit static electricity discharge from the soft fuzzy material of the outer layer to the mechanism 22.

The battery 28 is preferably rechargeable using an inductive charger. The inductive charger in one embodiment of the invention is a stool or chair shaped object upon which the care buddy 16 may be seated when recharging the battery 28 is necessary. The battery 28 provides power to the control circuitry 30 where the power is distributed to the various elements of the mechanism 22.

The motor assembly 26 includes an array of electric motors, mechanical linkages, solenoids and other components to control movement of the care buddy 16. This movement includes movements of appendages, eyes, mouth and other body parts of the care buddy 16 to enable the care buddy 16 to communicate via body language. The body language can include gestures, eye movement and facial expression and may occur during verbal communication.

The speech generator 34 is a computing device that includes memory and processing capability to generate acoustic speech from digital data. In an alternate embodiment speech generator 34 functions simply has an audio mixer to automatically assure that sounds generated by the care buddy 16 can be heard by the user. The communication interface 36 communicates speech or digital data to the speech generator 34. The communication interface 36 enables wireless communication between the care buddy 16 and the network 12 (FIG. 1).

The speech generator 34 has the ability to learn to mimic the voice of someone familiar to the user, and that frequently comes into proximity to the care buddy 16. The speech generate 34 detects speech from the person familiar to the user, selects a database of spoken words, modifies the spoken word database according to the tone, and pace of the familiar person's own speech. In this way, speech of the familiar person can be mimicked by the care buddy when communicating with the user to facilitate familiarity and an emotional bond.

In one embodiment, the speech detector 38 operates in a passive mode until speech is detected by the care buddy 16. Detecting speech triggers the speech detector 38 to operate an active mode. An active mode speech is captured by the communication interface 36.

In one embodiment, the recorded speech is communicated via the network 12 to the backend computing engine 14 for recognition. An alternate embodiment the communication interface 36 includes speech recognition capability using local computing capabilities.

Recognized speech is converted and simplified into a data set which is communicated to, and interpreted by, the backend computing engine 14 via the network 12. Through the use of artificial intelligence and context recognition the recognized speech provides a basis for the backend computing engine 14 to generate a response.

The response is converted into a simplified data set which is then communicated by the backend computing engine 14 via the network 12 to the communication interface 36 of the care buddy 16. The communication interface utilizes the simplified data set and the speech generator 34 to communicate articulate speech via the speaker 24 two a user. The speech generated by the system 10 provides a sensible response to the user due to the advanced implementation of both context recognition and artificial intelligence.

Figure 3:
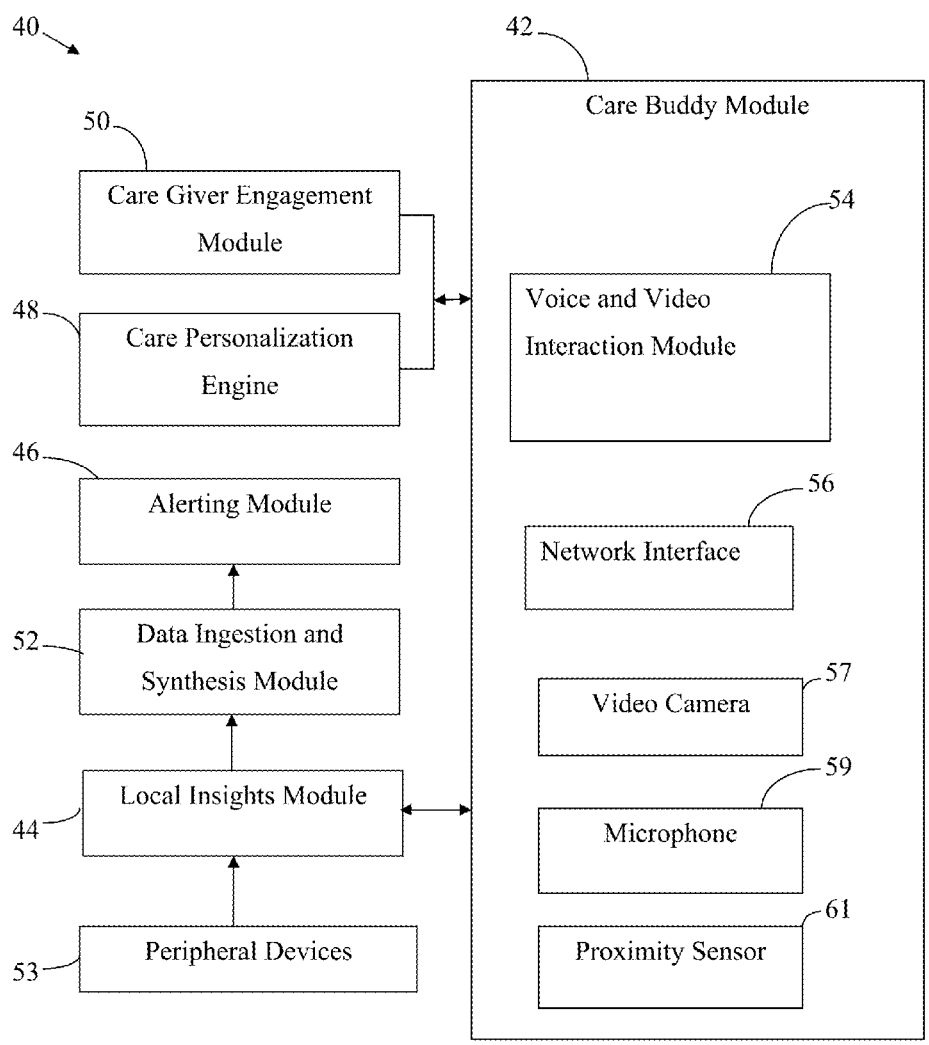
FIG. 3 is a component diagram in accordance with the present invention.

FIG. 3 shows a system in accordance with the present invention, generally designated with the reference numeral 40. The system 40 includes a care buddy module 42. The module 42 is integrated with the mechanism 22 of the care buddy 16. The module 42 includes a voice and video interaction module 54, a network interface 56, a video camera 57, a microphone 59, and a proximity sensor 61. The module 54 enables real time intelligent interaction between a user and the care buddy 16. The network interface 56 enables remote communication between the user and the network 12.

The local insights module 44 utilizes information locally in real time including communicating with local sensors, and pre-programmed reactions. Alerts can be immediately delivered. Where the network is not operational or not accessible, the local insights module functions independently of the network. The local insights module 44 communicates with peripheral devices and responds to generate alarms, etc.

The care personalization engine 48 is protected with respect to privacy. Personal observations including personal habits and routines need not be processed at back end in addition to certain video information. Data that can directly be associated with an identifiable individual can be separated from the back end backend computing engines through the use of a firewall.

Care giver engagement module 50 notifies a care giver in response to changes such as deterioration of a user's mood, movement or other conduct including sentiment in voice, voice volume, video of user's face, vocalization of needs regarding physical condition. The care giver engagement module 50 shares data with doctor or other care giver and may send alerts to a care giver when appropriate. Responses from the care giver may be recorded and played back, or presented in real time through the care buddy, or the user interface.

Data ingestion and synthesis module 52 sits behind the local insights module and communicates with the peripheral devices. All data is collected with this.

The care buddy module 42 is in operative communication with a local insights module 44 that enables context recognition, and alerting module 46 that enables the care buddy module 42 to communicate health or safety related alerts to a care giver. The personalization engine 48 that determines personalized care instructions that can be communicated to the user by the system or a care giver.

The system 40 also includes a caregiver engagement module 50 that combines verbal communication with robotic body language and gestures to enable the care buddy module 42 to better communicate with the user.

A data ingestion and synthesis module 52 is included with the system 42 enable the care buddy module 42 to gather data. The module 52 is responsible to leverage advanced analytics and insights generation capabilities to derive both across patient population clusters/segments as well as at individual user levels.

Gathered data includes optical data, audio data, proximity data and health monitoring data. The health monitoring data is gathered from peripheral devices 53, which can include a single device or multiple biometric monitoring devices. A single wearable device may have numerous functionalities including biometric sensors.

Optical data is gathered by a video camera 59 within the care buddy 16. The video camera is controlled by the care buddy module 42. Audio data is gathered by the microphone 59. Proximity data is gathered by the proximity sensor 61.

The network interface 56 is adapted to communicate with the peripheral devices 53 as well as the network 12. In one embodiment of the invention, peripheral devices 53 include at least one peripheral device such as a fixed standalone device that tracks activities of a user to assure safety. The peripheral devices 53 includes a visual sensor for directly or indirectly sensing the position of the user and its movements relative to objects in the location of the user.

In another embodiment, the peripheral devices include a wearable device that can be worn by a user and having various functionalities. For example a wearable device may wrap about the wrist of a user to detect blood pressure, heart rate $SpO_2$ (oxygen saturation), or other blood gas analyzer. Peripheral devices 53 that are locally positioned (within a communicative proximity to the care buddy 16 and the user) to communicate locally with the care buddy 16 via the network interface 56.

Peripheral device 53 include a blood pressure monitor, a temperature sensor, a heart rate monitor, blood glucose monitor, a breathing monitor, a blood oxygen sensor, and any other device normally utilized in an institutional healthcare setting.

In one embodiment the peripheral devices 53 include a microchip embedded in the skin of a user, or swallowed, to detect health data. The microchip includes a micro-transmitter at low power and a signal booster patch that is worn on the body, such as on the abdomen so that the micro-transmitter power can be kept at save levels. The microchip communicates through the body to the micro-transmitter that transfers data detected by the microchip to the care buddy 16. Preferably the microchip is an ingestible sensor device that may be swallowed to diagnose one or more conditions of the user, and to monitor health data.

The ingestible sensor device may include a sensor configured to receive a stimulus inside the gastrointestinal tract of the user. The sensor is configured to transmit an acoustic signal. A sensor link module may be located on the surface of the user to receive the acoustic signal output by the sensor, or the sensor link module is a wearable device 53.

A typical peripheral device 53 communicates locally with the network interface 56. This communication is, for example, via a local area network, or uses a Bluetooth protocol, or a radio frequency communication protocol. The peripheral device includes a scale for detecting user weight and the scale communicates wirelessly with the care buddy. In another embodiment the peripheral device is an activity monitor that monitors various user activity including counting steps walked.

Wearable devices offer the advantage of assisting in the collection of proximity data relative to the user by the care buddy 16. Wearable devices offer the advantage of being adapted to look like jewelry, a wristwatch, or other accessory. It is important that the local peripheral devices are utilized and therefore offering wearable devices as fashion accessory options overcomes challenges in maintaining optimal data collection. The wearing of such wearable devices improves a user's emotional well being by avoiding the stigma of carrying health monitoring equipment in an obvious and incontinent manner. This yields social confidence and emotional well-being.

A wearable device can be programmed to synchronize with the care buddy 16 and communicate in real time when in proximity with the care buddy 16. Such a wearable device can record data when not in proximity with the care buddy 16. In this way data can continuously be collected and periodically uploaded.

Various embodiments of wearable devices include fashionable garments with an embedded RFID chip, earrings, pendants, hearing aids, headbands or other headdress, a wristwatch or any other fashion accessory enabling a remote non-intrusive patient monitoring platform.

The utilization of peripheral devices to capture patient (or user) data yields a system 40 that is functional, scalable, highly adaptable to the needs of the user, and reduces the expense of hardware required to enable the care buddy to function.

It can be appreciated that the peripheral devices can be typical networked smart household appliances that may pose a danger if left on, or are not monitored. Users having early stage dementia may require assistance under some circumstance in remembering to turn off the stove, water, or other household appliance or service. If the tap, stove or other appliance with properly equipped with communication hardware, these can function as peripheral devices 53 in the system 40. Accordingly, a user that suffers from early stage memory loss and is normally unassisted by other humans, can delay or avoid a move from a home environment to an assisted living environment by utilizing the present invention. Also users that tend to be forgetful can achieve a higher degree of safety in a home environment.

In one embodiment the data ingestion and synthesis module 52 includes context recognition to enable the care buddy module 42 to observe normal everyday activities within a user's home. These normal activities include cooking or operating a faucet, for example. Should a cooking pot boil over, a stove burner be left on for too long, or a faucet be left running the local insights module 44 can detect such a problem and in cooperation with the alerting module 46 generate a signal via the care buddy module 42 that enables the care buddy 16 to alert the user via gestures and speech and further escalate the alert appropriately to the people in the user's extended care network such as family, friends, neighbors, and others.

In an alternate embodiment, peripheral devices 53 can include a smoke detector, carbon monoxide detector, an entry door lock and other peripheral devices 53 that can pertain to safety and security.

In some instances a user may be challenged to hear, or be completely deaf. Under such circumstances the care buddy can react with blinking eyes, lights and moving appendages to alert a user of a safety or security issue.

In other instances, a forgetful user may neglect to close a car door or a front entryway door. Similarly the care buddy 16 can react verbally or through choreographed movement to alert the user. These types of interactions build a relationship between the care buddy 16 and the user and makes the user feel emotionally secure, safe and looked-after. The care buddy 16 is also capable of casual conversation, which over time, may also build an emotional relationship with the user as found in several research studies.

With the relationship built, the care buddy 16 can help with compliance with recommended health care plans and schedules that a user has set or has been set for the user. For example, a care buddy 16 can monitor the periodic consumption of pharmaceuticals by a user. At an appointed time, should the user fail to administer the pharmaceuticals, the care buddy 16 may offer a friendly reminder. This feature assures compliance with physician or care giver recommended "Care plans" including pharmaceutical schedules and broader care plan items like diet, exercise, appointments with labs/radiology/other care givers etc. This feature can also assure compliance with normal hygiene including tooth brushing, flossing, shaving and bathing. Even the bed time or waking routine can be monitored by the careful observations of the care buddy 16, utilizing pattern recognition and context recognition, to generate a reminder to the user. The user schedule can also be managed through conversation with the care buddy 16. In this way doctor's appointments, or scheduled social appointments with friends and family are not missed.

The care personalization engine 48 enables "personalization" of communication between the care buddy 16 and a user. The care buddy 16 along with the backend computing engine 14 have a secure personalization engine that constantly learns and refines its understanding of the user, its habits and communication preferences. It constantly leverages this personalization engine to have engaging conversations with the user.

The local insights module 44 leverages specific insights generated from the backend computing engine 14 but also uses local interaction with the user to derive patient specific insights to further improve communication quality between the care buddy 16 and the user.

The care personalization engine 48 leverages all of the data, including learned data, about a user and then customizes a care delivery procedure to personalize communication associated with any care delivery process.

The data ingestion and synthesis module 50 utilizes data captured thru the direct user interactions with the care buddy. This includes body language, facial gestures, speech, proximity and user activity data. The module 50 further utilizes all relevant data from the computer 14 and backend computing engine that is required for the generation of the local insights as well as for the care personalization.

Figure 4:
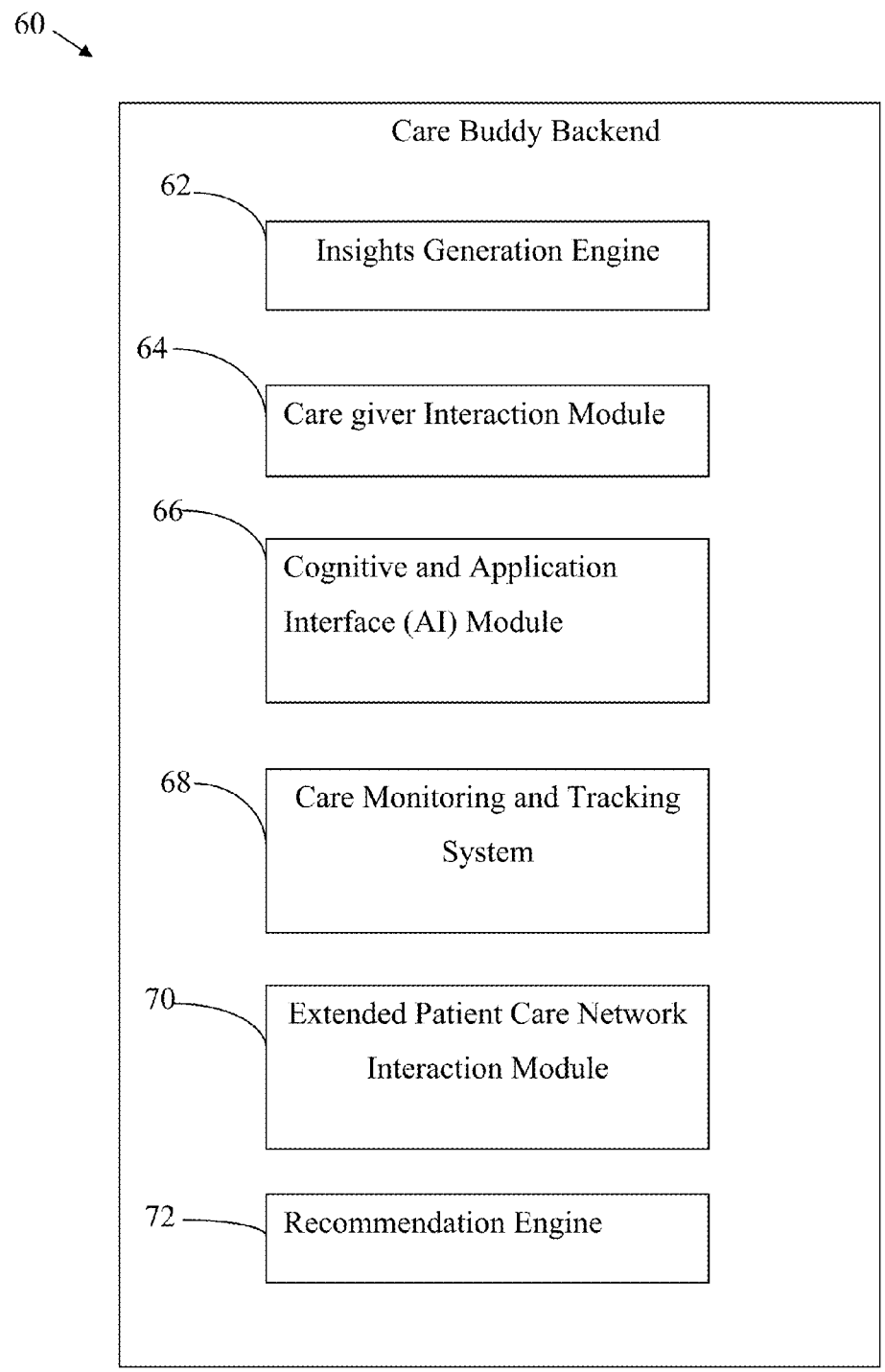
FIG. 4 is a component diagram of a backend of the system of the present invention.

FIG. 4 is a system generally designated with the reference numeral 60. The system 60 is characterized as the care buddy backend computing engine. The system 60 is implemented by the backend computing engine 14 which has sufficient computing capacity to operate the various modules of the system 60. The system 60 includes and insights generation engine 62, a caregiver interaction module 64, a cognitive an application interface module 66, a care monitoring and tracking system 68, an extended patient care network interaction module 70, and a recommendation engine 72.

The system 60 includes the data ingestion and synthesis module 52 shown in FIG. 3. The modules of system 60 enable the application of machine learning, advance analytics and artificial intelligence capabilities like context recognition, facial expression recognition, body language recognition, data monitoring, and interaction formulation and execution. These modules of the system 60 are preferably implemented in software. It can be appreciated however that each of these modules can be executed on distributed computers located in various nodes of the network 12.

The recommendation engine 72 leverages available datasets to derive and deliver recommendations to the user via the care buddy system. The recommendation engine 72 personalizes the care buddy system by customizing communications to a specific user.

Figure 5:
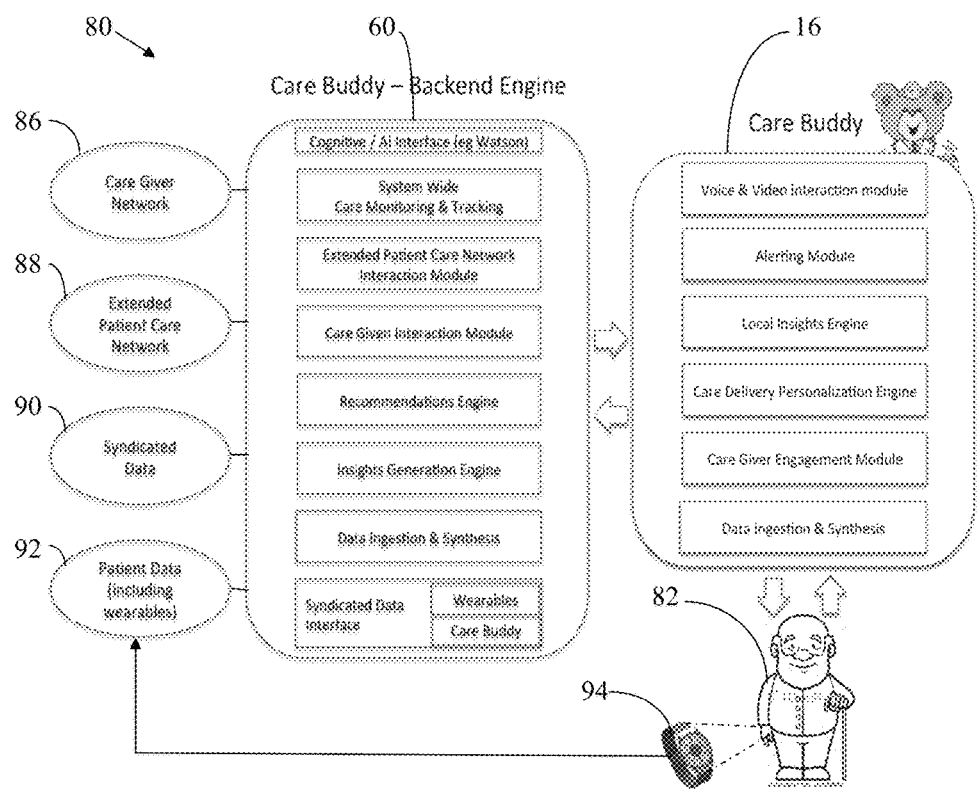
FIG. 5 is a system diagram in accordance with the present invention.

FIG. 5 is a system generally designated with the reference numeral 80. The system 80 includes a care buddy 16 and the care buddy back end 60. The back end 82 communicates with, or utilizes, a caregiver network 86, an extended patient care network 88, syndicated data 90 and patient data 92. The care buddy 16 communicates directly with the user 82. Syndicated data 90 includes any third party data assembled in any way such as a smart phone application. In one embodiment, syndicated data includes a diet log. In another embodiment, syndicated data includes health club activities logged by a third party smart phone application.

The backend 82 is software programmed to run on the backend computing engine 14 of FIG. 1. with the cognitive or artificial intelligence interface. An example of an artificial intelligence interface is the IBM Watson® computing platform. In addition to data gathered by through the care buddy 84 and its peripheral devices 53, various disparate information is relied upon. This information includes care giver network 86 data including diagnostic and therapeutic recommendations, extended patient care network 88 data including communication access between the patient 82 to a patient care professional, and syndicated data 90 that is stored in databases and accessed by the backend 60. Syndicated data 90 includes research topics that are integral to the performance of the system 80. Patient data 92 is derived by observation of the patient by the care buddy 16 and through the peripheral devices 53.

In one embodiment, the user 82 includes a wearable device 94. The wearable device 94 communicates patient data to the backend 60 directly in one embodiment of the invention, or via the care buddy 16 in another embodiment of the invention.

Data collected with the figurine and peripheral devices, including wearable devices are used to detect care plan adherence when the user has been offered a health care plan. Observations of the user's actions, biometric data collected from the peripheral devices, conversations between the figurine and the user, and other data are used to anticipate deviations from the care plan and provide remedies for anticipated deviations from the plan as well as actual deviations from the plan. Remedies for such deviations include conversational queries from the figurine, escalation to a health care provider, who can either telephonically contact the user, or communicate via the user interface via audio and video.

In one embodiment of the invention, when deviation from the care plan is detected, the deviation is analyzed by the backend computing engine to determine its materiality, and to formulate a response based in part on the materiality of the deviation, the number of prior times and frequency that a deviation is detected, and biometric data indicating health concerns. Escalation enables the backend computing engine to generate a message to a predetermined health care provider and/or to the extended care network, who can also formulate a response to the deviation.

The system 80 is enabled by a local and remote computing resources including the back end computing engine 14 with advanced analytics and artificial intelligence capabilities to analyze data pertaining to the user and its environment as well as the aggregated patient data across all the user populations to derive actionable insights and enable the robotic figurine to deliver messages/instructions to the end user to achieve "care plan" adherence. While the instant description is intended to provide examples of the present invention, the scope of the present invention is defined particularly by the appended claims.

We claim:

1. A health care delivery and monitoring system, comprising:
   a robotic figurine having a mechanism including an audio interface, a speaker, a means for enabling robotic movement, a rechargeable power source, control circuitry, a video camera, a speech generator, a communication interface, a network interface, a local computation module and a speech detector operatively connected with each other;
   the robotic figurine includes eyes and an outer layer and stuffing, the stuffing surrounds a portion of the mechanism to protect it from impact and temperature changes;
   the network interface being connected via a network to a computer for providing back end data management and computing capacity;
   whereby the video camera enables the robotic figurine to observe a user and communicate observations to the computer, the computer generates instructions and communicates the instructions to the robotic figurine to enable the robotic figurine to communicate with the user;
   a client interface with a video terminal in communication with the figurine to provide supplemental communication to the user; and
   wherein video terminal streams are produced by a projector embedded in the robotic figurine, the projector generates a projection that is viewable by the user in two dimensions, the video terminal streams further include three dimensional images generated by a device capable of producing three dimensional images, where both the projector and the three dimensional video device are in operative communication with the back-end computer.

2. The system as set forth in claim 1, wherein the instructions generated by the computer include gestures and voice communication.

3. The system as set forth in claim 2 further comprising:
   a wearable device in wireless communication with the communication interface for collecting health data of the user, the wearable device being attachable to the user and being capable of gathering biometric data of the user, and
   wherein the computer combines biometric data from the wearable device and syndicated data to generate gestures and voice communication to the user.

4. The system as set forth in claim 1, wherein the battery is rechargeable by induction.

5. The system as set forth in claim 1, wherein the figurine includes eyes that move and a motor assembly moves the eyes during communication with the user.

6. The system as set forth in claim 1, wherein the figurine includes appendages that move and a motor assembly moves the eyes during communication with the user.

7. The system as set forth in claim 1, wherein the figurine includes moveable eyes, a mouth, and appendages that move;
   the speaker communicates verbally with the user;
   the motor assembly moves the eyes, mouth and appendages during verbal communication with the user.

8. A method for health care delivery and monitoring comprising:
   providing a robotic figurine having components including: a speaker, a motor assembly, a battery, control circuitry, a video camera, speech generator, a communication interface, a network interface and a speech detector operatively connected with each other; the robotic figurine includes an outer layer, and stuffing;
   collecting data associated with a user using the figurine, the data being selected from the group consisting of, biometric, activity, speech, video data, and combinations thereof;
   collecting data from peripheral devices including a weight scale;

collecting data about the user from other syndicated data sources; communicating the collected data to the backend computer for processing;

using the backend computer for generating verbal communication between the figurine and the user;

providing a client interface with a video terminal in communication with the figurine to provide supplemental communication to the user; and wherein video terminal streams are produced by a projector embedded in the robotic figurine, the projector generates a projection that is viewable by the user in two dimensions, the video terminal streams further include three dimensional images generated by a device capable of producing three dimensional images, where both the projector and the three dimensional video device are in operative communication with the backend computer.

9. The method of claim 8, wherein the figurine and the backend computer leverages capabilities both locally and remotely to analyze data specific to the user as well as aggregate data.

10. The method of claim 8, wherein the video terminal depicts a care provider and streams a care plan including verbal and visual communication from the care provider.

11. The method of claim 10, wherein the backend computer and the figurine cooperate to utilize data collected with the figurine to develop and communicate the care plan, the care plan including at least one plan selected from the group consisting of: medication plan, diet plan, exercise plan, vitals/health measurement plan, appointment schedule.

12. The method of claim 11, wherein the data collected with the figurine is used to detect care plan adherence, and to anticipate deviations from the care plan.

13. The method of claim 12, wherein if any deviation from the care plan is detected, analyzed by the backend computer, which can escalate the deviation by communication the deviation to a health care provider or to an extended care network team that include family, friends, or neighbors.

14. A health care delivery system, comprising:

a robotic figurine having a mechanism including an audio interface, a speaker, a means for enabling robotic movement, a rechargeable power source, control circuitry, a video camera, a speech generator, a communication interface, a network interface, an ingestible sensor and a speech detector operatively connected with each other;

the robotic figurine includes an outer layer and stuffing, the stuffing surrounds a portion of the mechanism to protect it from impact and temperature change;

the ingestible sensor capable of operating within a user to gather biometric data, the ingestible sensor being in communication with the network interface;

the network interface being connected via a network to a computer for providing back end data management and computing capacity;

whereby the video camera enables the robotic figurine to observe the user and communicate observations to the computer, the computer generates instructions and communicates the instructions to the robotic figurine to enable the robotic figurine to communicate with the user;

a client interface with a video terminal in communication with the figurine to provide supplemental communication to the user; and wherein video terminal streams are produced by a projector embedded in the robotic figurine, the projector generates a projection that is viewable by a user in two dimensions, the video terminal streams further include three dimensional images generated by a device capable of producing three dimensional images, where both the projector and the three dimensional video device are in operative communication with the backend computer.

15. The system as set forth in claim 14, wherein the ingestible sensor is ingestible into the digestive tract of a user and is enabled to communicate acoustically with an amplifier, the amplifier being in communication with the network interface.

* * * * *